United States Patent [19]

Monestere

[11] Patent Number: 4,838,413
[45] Date of Patent: Jun. 13, 1989

[54] CONTACT LENS DISINFECTION CASE WITH LOCKING MECHANISM

[75] Inventor: Martin Monestere, Kendall Park, N.J.

[73] Assignee: Allergan, Inc., Irvine, Calif.

[21] Appl. No.: 99,188

[22] Filed: Sep. 21, 1987

[51] Int. Cl.⁴ ............................................. A45C 11/00
[52] U.S. Cl. .................... 206/5.1; 220/315; 220/324; 134/137
[58] Field of Search .................. 206/1.5, 5.0, 5.1, 807; 215/219, 220, 207, 367; 220/315, 324, 325, 320; 134/137, 143, 166 R

[56] References Cited

U.S. PATENT DOCUMENTS

| | | |
|---|---|---|
| 3,939,968 | 2/1976 | Ryder . |
| 3,977,517 | 8/1976 | Kadlecik et al. . |
| 3,990,579 | 11/1976 | Manning . |
| 3,997,049 | 12/1976 | Sherman . |
| 4,011,941 | 3/1977 | Parsons . |
| 4,143,116 | 3/1979 | Meltzer . |
| 4,396,583 | 8/1983 | LeBoeuf . |

Primary Examiner—David T. Fidei
Attorney, Agent, or Firm—George A. Skoler; Vincent P. Pirri; James M. Kanagy

[57] ABSTRACT

A contact lens disinfection case includes a hollow cylindrical body with two open ends, and first and second end caps mounted on the open ends of the body to define with the body a fluid-tight housing. A contact lens holding basket is mounted on and is removable with the first end cap. An elongate locking member extends through the hollow body and engages the first and second end caps when the end caps are mounted on the body. The second end cap, when mounted on the body, abuts against the elongate locking member and causes is to engage the first end cap, locking it in place and preventing its removal. When the second end cap is not mounted on the body, the elongate locking member is positionable in non-engagement with the first end cap, allowing the first end cap to be removed from the hollow body.

14 Claims, 2 Drawing Sheets

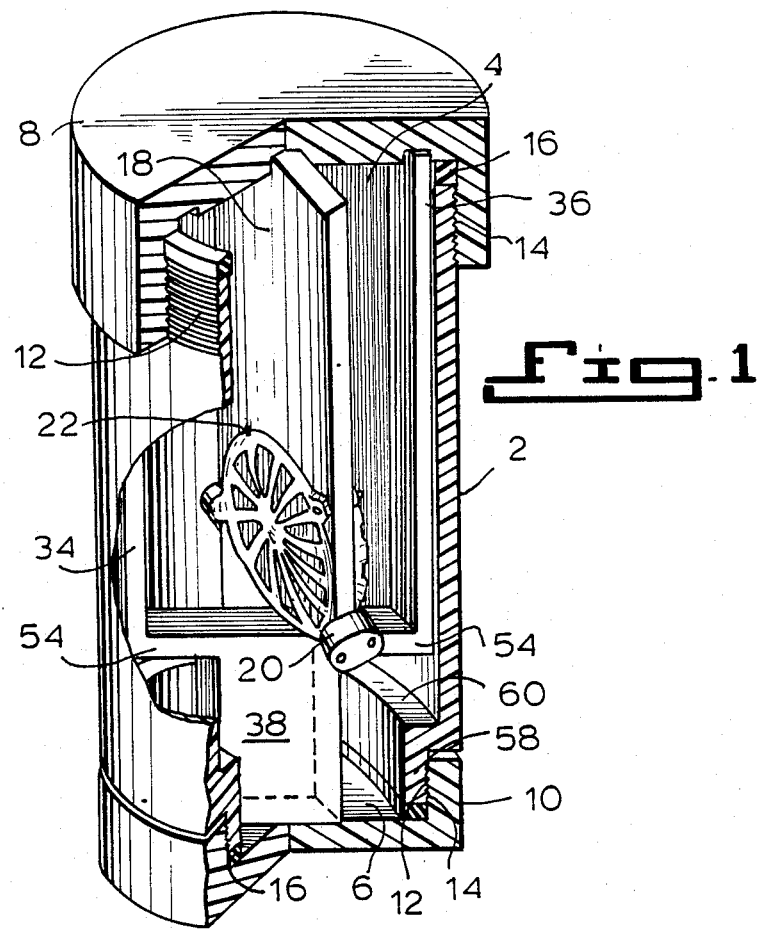
Fig. 1
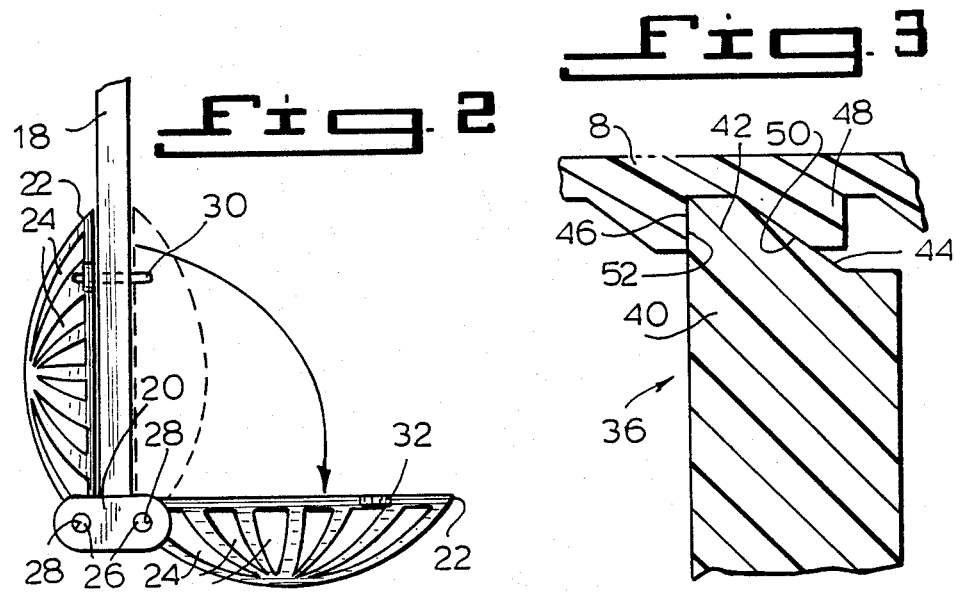
Fig. 2
Fig. 3

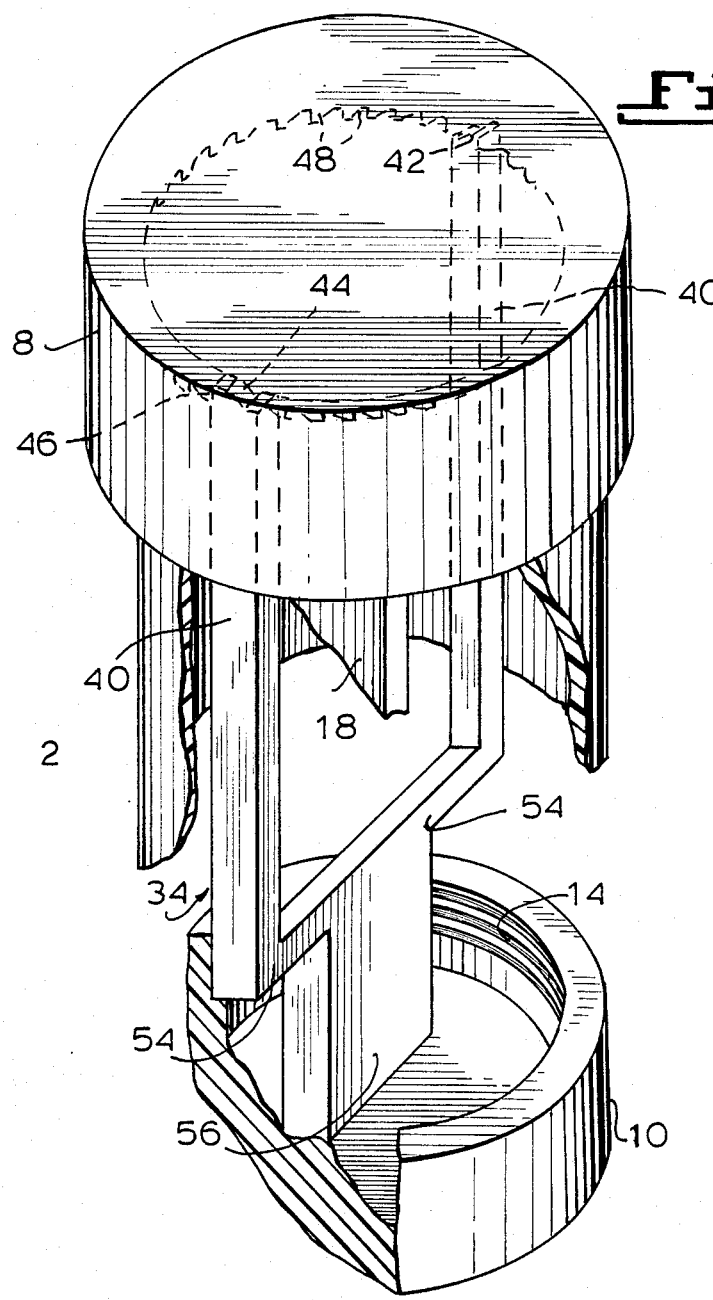

CONTACT LENS DISINFECTION CASE WITH LOCKING MECHANISM

BACKGROUND OF THE INVENTION

1. Field of the Invention

The present invention relates to a contact lens disinfection case, and more particularly relates to a contact lens disinfection case with a locking mechanism that deters the user from opening the case before a neutralizing solution has been added.

2. Description of the Prior Art

Many contact lens disinfection cases on the market today have only one opening with a removable cap covering the opening. The cap is removed and the contact lenses are placed in the case and held in a basket or other device disposed within the case. A sterilizing solution, such as hydrogen peroxide, is then added to the case through the opening. The cap is then replaced on the case. After a certain time has elapsed, the cap is removed and the hydrogen peroxide solution is emptied from the case. A saline or other solution is then added to the case, which solution neutralizes the residual hydrogen peroxide.

One of the inherent disadvantages of the type of lens disinfection case described above is that oftentimes the user forgets to add the neutralizing solution or thinks he has added the neutralizing solution when in fact he has not. The residual hydrogen peroxide remaining on the lens which is not neutralized will cause discomfort and irritation to the eye.

OBJECTS AND SUMMARY OF THE INVENTION

It is an object of the present invention to provide a contact lens disinfection case which helps prevent accidental removal of the contact lenses from the case before the sterilizing solution is neutralized.

It is another object of the present invention to provide a contact lens disinfection case which prevents the user from reusing the sterilizing and neutralizing solutions.

It is a further object of the present invention to provide a contact lens disinfection case which stores and maintains the lenses in a disinfected condition until ready for use.

It is a still further object of the present invention to provide a contact lens disinfection case which overcomes the inherent disadvantages of known disinfection cases.

In accordance with one form of the present invention, a contact lens disinfection case includes a hollow case body having two opposite open ends. First and second end caps are screw mounted onto the open ends. Together the hollow case body and end caps define a fluid-tight housing for receiving the sterilizing and neutralizing solutions.

A pair of baskets are disposed in the body, and may be mounted on the first end cap and removable with it. The baskets are used to hold the contact lenses in the case.

The contact lens disinfection case further includes a locking mechanism which prevents the first end cap from being removed while the second end cap is mounted on the case body. The locking mechanism in one form is an elongate member which extends through the hollow case body between the end caps. When the second end cap is mounted on the body, it abuts against and forces the elongate locking member to assume a position where it engages the first end cap and prevents the end cap from being unscrewed from the case body. When the second end cap is removed, the elongate locking member may be grasped by the user and pulled from engagement with the first end cap, allowing the first end cap to be unscrewed and removed from the hollow case body.

To use the disinfection case, the second end cap is mounted on the case body, and the first end cap and baskets are removed. The contact lenses are placed in the baskets, and a sterilizing solution is added to the case body through the uncovered end. The first end cap is then replaced on the body.

The locking mechanism allows the first end cap to be turned only in a direction which tightens it onto the case body; the end cap may not be unscrewed in the opposite direction.

After sufficient time has elapsed for the contact lenses to be fully sterilized, the second end cap is removed and the sterilizing solution is allowed to drain from the case. The case is then turned upside down and refilled with a saline or other neutralizing solution. The second end cap is then remounted on the case body.

Again, after sufficient time has elapsed, the second end cap is removed and the neutralizing solution is drained and discarded. The user then pulls the locking mechanism towards the open end where it no longer engages the first end cap, and the first end cap is removed and with it the baskets holding the contact lenses.

As mentioned previously, the baskets are mounted to the first end cap. In the preferred form of the invention, therefore, the contact lenses are not accessible through the opening covered by the second end cap (i.e., through which the neutralizing solution is added). Accordingly, it is only after the neutralizing solution has been added and the entire case drained of solution that the contact lenses may be removed from the disinfection case.

Preferred forms of the disinfection case, as well as other objects, features and advantages of the present invention, will become apparent from the following detailed description of illustrative embodiments thereof, which is to be read in connection with the accompanying drawings.

BRIEF DESCRIPTION OF THE DRAWINGS

FIG. 1 is a perspective view, partially broken away, of a contact lens disinfection case formed in accordance with the present invention.

FIG. 2 is a side view of the baskets used to hold the contact lenses within the disinfection case.

FIG. 3 is a partial sectional view of the locking mechanism used in the disinfection case.

FIG. 4 is a perspective view, fragmented and partially broken away, of the disinfection case, showing a preferred form of the locking mechanism.

DETAILED DESCRIPTION OF THE PREFERRED EMBODIMENTS

Referring initially to FIG. 1 of the drawings, it will be seen that a preferred form of a contact lens disinfection case constructed in accordance with the present invention includes a hollow cylindrical case body 2. The body 2 includes a first open end 4 and a second open end 6 opposite the first end. As will be described, a sterilizing solution is poured into the hollow case body 2 through the first open end 4, and later, a neutralizing solution is poured through the second open end 6.

A first end cap 8 is removably mounted on the first open end 4 of the hollow case body, and similarly, a second end cap 10 is removably mounted on the second open end 6. Preferably, each end cap is screw threaded onto the hollow case body. For this purpose, portions 12 of the outer peripheral surface of the hollow body 2 surrounding the open ends are threaded. Similarly, an internal surface 14 of each end cap 8,10 is threaded. The threaded surfaces of the hollow case body 2 and the two end caps 8,10 engage one another so that the end caps may be screwed onto the hollow case body by turning them in a tightening direction, or unscrewed from the body by turning them in an opposite, loosening direction.

Together the hollow caes body 2 and the first and second end caps 8,10 define a fluid-tight housing to receive the contact lenses and the sterilizing and neutralizing solutions. To ensure fluid tightness, the end caps may carry gaskets 16 or seals, which gaskets 16 are situated so as to engage the edges of the hollow case body 2 that define the first and second open ends 4,6 when the end caps are screwed onto the hollow body.

The contact lens disinfection case of the present invention also includes structure for supporting the contact lenses within the hollow body. As shown in FIGS. 1 and 2, this structure includes a plate 18 mounted on the first end cap 8 and extending from the end cap in an axial direction. When the first end cap is mounted on the hollow case body 2, the plate 18 is suspended from the end cap in the interior of the body.

A transversely elongated, bulbous formation 20 is formed on each side edge at the bottom of the plate 18. Two baskets 22, each formed with radially extending apertures 24, are mounted between the bulbous formations 20 on opposite flat sides of the plate 18. The baskets 22 include pivot pins 26 which are received in holes 28 formed in the bulbous formations 20, and are pivotable toward and away from respective flat sides of the plate 18.

Each basket 22 is concave so that it can receive a respective left and right contact lens. Furthermore, the baskets may be marked with an L or an R to designate the particular contact lens that it holds.

The plate 18 may include a post 30 extending from each opposite flat side, and each basket 22 may include a pressure fitting 32 which is situated on the rim of the basket. When a contact lens is placed in each basket, the baskets may be swung upwardly against the opposite flat sides of the plate 18 and secured against the plate by the pressure fitting 32 of each basket receiving and holding its respective post 30. Thus, the contact lenses may be removably supported by the baskets 22 mounted on the plate 18, and exposed to the sterilizing and neutralizing solutions through the apertures 24 formed in the baskets when the first end cap 8 is mounted on the hollow case body.

The contact lens disinfection case of the present invention also includes a locking mechanism which prevents the first end cap 8 from being unscrewed and removed while the second end cap 10 is mounted on the case body 2. The locking mechanism is basically an elongate member 34 having opposite first and second ends 36,38 which engage the first and second end caps 8,10, respectively, when the end caps are mounted on the hollow case body 2.

More specifically, the elongate locking member 34 is slidable axially through the hollow case body between two positions. When the second end cap 10 is mounted on the hollow body 2, its inside surface abuts against the second end 38 of the elongate locking member 34 and forces it upwardly into one position where its first end 36 engages the first end cap 8 and prevents the first end cap from being unscrewed. When the second end cap is removed from the hollow case body, the elongate locking member 34 is exposed and may be pulled downwardly by the user so that its first end 36 is no longer in engagement with the first end cap 8, allowing the first end cap to be unscrewed and removed from the hollow case body 2.

In a preferred form of the invention, as shown in FIGS. 3 and 4, the first end 36 of the elongate locking member includes a pair of parallel, upstanding arms 40 which are spaced apart from each other. Each arm 40 includes at least one pawl tooth 42 projecting from its top. Each pawl tooth 42 includes a ramp-like surface 44, and a shoulder 46 adjacent or close to the ramp-like surface and defining the side of the tooth.

Similarly, a plurality of ratchet teeth 48 are formed in the inner surface of the first end cap 8, which ratchet teeth 48 are aligned with the pawl teeth 42 of the elongate locking member when the first end cap is mounted on the hollow case body. Each ratchet tooth 48 includes a ramp-like surface 50 and shoulder 52 adjacent or close to the ramp-like surface and defining the side of the tooth so that the first end cap 8 is provided with a series of alternating shoulders and teeth.

Together the pawl teeth 42 of the elongate locking member 34 and the ratchet teeth 48 of the first end cap 8 define a uni-directional coupling which, when the two are engaged, allows the first end cap to be turned only in a tightening direction.

As clearly shown in FIGS. 3 and 4 of the drawings, when the first end 36 of the elongate locking member engages the first end cap 8 (which occurs when the second end cap 10 is mounted on the case body 2), the ramp-like surfaces 44,50 of the ratchet teeth and pawl teeth slidably engage one another as the first end cap is turned in a tightening direction. However, when the user tries to remove the first end cap 8 by turning it in a loosening direction, the shoulders 46,52 of the ratchet teeth and pawl teeth abut against one another and prevent the end cap 8 from turning.

When the second end cap 10 is not mounted on the hollow case body 2, the elongate locking member 34 may be positioned by the user so that the pawl teeth 42 no longer engage the ratchet teeth 48 of the first end cap. This allows the first end cap to be unscrewed and removed from the case body.

The elongate locking member, in its preferred form, further includes a transverse cross member 54 having opposite ends on which the upstanding arms 40 are mounted perpendicularly, and has its second end 38 formed as a tab 56 extending downwardly from the transverse cross member 54 and projecting far enough towards the second open end 6 of the hollow body so as to engage the second end cap 10 mounted on the body and so that the user may grasp it and pull the locking member out of engagement with the first end cap after the second end cap has been removed.

The particular preferred form of the elongate locking member 34, with its transverse cross member 54 and upstanding arms 40, provides the locking member with a certain amount of longitudinal resiliency so that the locking member gives under sliding engagement with the ratchet teeth 48 when the first end cap 8 is screwed onto the case body 2, and yet the locking member biases the pawl teeth 42 upwardly between adjacent ratchet teeth 48 so that the shoulders 44,50 of each abut against one another when the first end cap 8 is attempted to be turned in a loosening direction.

As shown in FIG. 1, the case body 2 may be formed with a neck 58 surrounding the second open end 6, which neck 58 may be of smaller radius than the rest of the body. In this way, the neck defines a ledge 60 formed inwardly of the case body. The ledge 60 acts as a stop to limit the downward travel of the elongate locking member 34. As the user pulls the tab 56 of the elongate locking member to disengage the pawl teeth 42 from the ratchet teeth 48 of the first end cap, the cross member 54 abuts against the ledge 60 formed in the hollow body. The ledge 60 is situated in the case body so that the locking member 34 has sufficient travel to disengage from the first end cap 8 but yet is held captive within the case body.

The first step in using the contact lens disinfection case of the present invention is to ensure that the second end cap 10 is securely mounted on the hollow case body 2, with the first end cap 8 removed from the body. The contact lenses are placed in their respective baskets 22, and the baskets are swung upwardly and locked against the sides of the plate 18. The hollow body 2 is filled with a sterilizing solution, such as hydrogen peroxide. The first end cap 8 with the lens holding baskets attached is then screwed onto the first open end 4 of the case body. Because the second end cap 10 is mounted on the case body, the first end cap 8 may only be turned in a tightening direction; it may not be unscrewed because of the engagement of the pawl teeth 42 with the ratchet teeth 48.

After sufficient time has elapsed for the contact lenses to be sterilized, the second end cap 10 is unscrewed from the case body and removed, and the sterilizing solution is drained. The case body is then refilled with a saline or other neutralizing solution, and the second end cap is then remounted on the case body.

After sufficient time has been provided for the saline solution to neutralize the residual hydrogen peroxide remaining on the contact lenses, the second end cap 10 may be removed, and the hollow case body 2 emptied of neutralizing solution. The user then grasps and pulls down on the tab 56 of the elongate locking member 34 until its cross member 54 abuts against the ledge 60 formed in the case body. With the locking member in this position, the pawl teeth 42 are no longer in engagement with the ratchet teeth 48 of the first end cap, and the first end cap 8 may be unscrewed and removed with the lens holding baskets 22 from the hollow body. The baskets may then be pivoted away from the plate 18, and each contact lens removed from its respective basket.

Because the lens holding baskets 22 are preferably securely mounted to the first end cap 8, the lenses are not accessible when only the second end cap 10 is removed. Furthermore, the first end cap 8 may not be removed as long as the second end cap 10 remains mounted on the hollow body. Thus, both end caps must be removed to get to the contact lenses. Such structure ensures that the case body 2 is completely drained of sterilizing and neutralizing solutions, preventing the reuse of such solutions, before the contact lenses may be removed from the case. By also locking the first end cap 8 (to which the lens holding baskets 22 are attached) to the case body 2, the particular structure of the disinfection case of the present invention helps remind the user to add neutralizing solution through the second end cap 10 to complete the disinfection process.

The disinfection case of the present invention is simple in construction and easy to assemble and clean. Its small size is perfectly adapted for not only disinfecting the contact lenses, but also maintaining and storing the contact lenses in a disinfected condition until ready for use.

Although illustrative embodiments of the present invention have been described herein with reference to the accompanying drawings, it is to be understood that the invention is not limited to these precise embodiments, and that various other changes and modifications may be effected therein by one skilled in the art without departing from the scope of spirit of the invention.

What is claimed is:

1. A contact lens disinfection case, which comprises:
    a fluid-tight housing, the housing having two open ends and first and second end caps removably mounted on the open ends;
    means for removably supporting a contact lens in the housing; and
    means for selectively locking the first end cap to the housing and for preventing the removal thereof when the second end cap is mounted on the housing, said locking means being formed as an elongate member having a first end adapted to engage the first end cap, and an opposite second end adapted to engage the second end cap, the first end being in engagement with the first end cap when the first and second end caps are mounted on the open ends of the housing.

2. A contact lens disinfection case as defined by claim 1, wherein each of the first end cap and housing threaded surfaces which engage one another to allow the first end cap to be threadingly mounted on and removed from an open end of the housing by rotating the first end cap in opposite tightening and loosening directions, respectively; and wherein the locking means is selectively positionable within the housing in a first position, wherein the first end of the locking means engages the first end cap so that the first end cap is rotatable only in the tightening direction, and being selectively positionable in a second position, wherein the first end of the locking means and the first end cap are in non-engagement to allow the first end cap to rotate in at least the loosening direction.

3. A contact lens disinfection case as defined by claim 2 wherein the locking means is disposed in the first position when the second end cap is mounted on a corresponding open end of the housing, and adapted to be disposed in the second position when the second end cap is not mounted on the open end of the housing.

4. A contact lens disinfection case as defined by claim 3 wherein the first end cap includes at least one ramp-like surface and shoulder formed thereon; and wherein the first end of the locking means has formed thereon at least one ramp-like surface and shoulder, the ramp-like surfaces of the first end cap and locking means being adapted to slidably engage each other to allow the first end cap to rotate in the tightening direction, and the shoulders of the first end cap and locking means being adapted to abut against one another to prevent the first end cap from rotating in the loosening direction.

5. A contact lens disinfection case as defined by claim 3 wherein the first end cap includes a plurality of ratchet teeth formed on a surface thereof and defined as a series of alternating ramp-like surfaces and shoulders; and wherein the first end of the locking means includes a pawl tooth projecting therefrom and formed with a ramp-like surface and a shoulder situated near the ramp-like surface, the pawl tooth being adapted to engage the ratchet teeth of the first end cap when the locking means is in the first position to allow the first end cap to rotate in the tightening direction and to prevent the first end cap from rotating in the loosening direction, and being in non-engagement with the ratchet teeth when the locking means is in the second position to allow the first end cap to rotate in at least the loosening direction.

6. A contact lens disinfection case as defined by claim 1, wherein the first end of the locking means includes a pawl tooth formed thereon; and wherein the first end cap includes a plurality of ratchet teeth formed on the surface thereof, the locking means being positionable in a first position wherein the pawl tooth engages the ratchet teeth of the first end cap to prevent the removal thereof from the corresponding open end of the housing, and being positionable in a second position wherein the pawl tooth is in non-engagement with the ratchet teeth of the first end cap to allow the removal thereof from the open end of the housing.

7. A contact lens disinfection case as defined by claim 1, wherein the first end of the locking means includes a pair of parallel, upstanding arms spaced apart from each other, each arm having a free end and including a pawl tooth formed on its free end; and wherein the first end cap includes a plurality of ratchet teeth formed on a surface thereof, the locking means being positionable in a first position wherein each pawl tooth engages the ratchet teeth of the first end cap to prevent removal thereof from the corresponding open end of the housing, and being positionable in a second position wherein each pawl tooth is in non-engagement with the ratchet teeth of the first end cap to allow removal thereof from the housing.

8. A contact lens disinfection case as defined by claim 7, wherein the locking means includes a cross member, the upstanding arms being mounted substantially perpendicularly on opposite ends of the cross member; and wherein the second end of the locking means is formed as a tab extending downwardly from the cross member in a direction opposite to that of the upstanding arms.

9. A contact lens disinfection case as defined by claim 8, wherein the housing is formed with a ledge disposed inwardly of the housing, the ledge defining a stop limiting travel of the locking means within the housing, the cross member abuting against the ledge when the locking means is in the second position.

10. A contact lens disinfection case as defined by claim 1, wherein the lens supporting means is mounted on the first end cap and projects therefrom so as to be disposed in the housing when the first end cap is mounted on the corresponding open end of the housing.

11. A contact lens disinfection case as defined by claim 10, wherein the lens supporting means includes a plate mounted on the first end cap, and a pair of baskets pivotally mounted on opposite sides of the plate, each basket being adapted to receive a contact lens and having a plurality of apertures formed therein.

12. A contact lens disinfection case, which comprises:
a hollow body, the body having a first open end for receiving a contact lens sterilizing solution therethrough, and a second open end for receiving a neutralizing solution therethrough;
a first end cap removably mounted on the first open end of the body, and a second cap removably mounted on the second open end of the body, the body and the first and second end caps, when mounted on the body, defining a fluid-tight housing for holding a contact lens;
means for supporting the contact lens within the body, the lens supporting means being mounted on the first end cap and being removable therewith; and
means for selectively locking the first end cap to the body, the locking means being mounted on the body and being reciprocatingly movable therein between first and second positions, the locking means being adapted to engage the first and second end caps when the end caps are mounted on the body, the locking means being disposed in the first position in locking engagement with the first end cap to prevent the removal thereof when the first and second end caps are mounted on the body, and being adapted to be disposed in the second position in which the locking means is unlockingly disengaged from the first end cap to allow the removal thereof when the second end cap is not mounted on the body.

13. A contact lens disinfection case, which comprises:
a hollow cylindrical body, the body having a first open end and a second open end opposite the first open end, and having a threaded surface adjacent to the first open end;
first and second end caps removably mounted on the first and second open ends of the body, respectively, the first end cap having a threaded surface adapted to engage the threaded surface of the body so that the first end cap may be mounted and removed from the first open end of the body by rotating the first end cap in opposite first and second directions, respectively;
means for supporting a contact lens within the body, the lens supporting means being mounted on the first end cap and being removable therewith; and
means for selectively locking the first end cap to the body, the locking means extending axially through the body and being reciprocatingly movable therein between first and second positions, the locking means including opposite first and second ends which are adapted to engage the first and second end caps, respectively, when the end caps are mounted on the body, the locking means being disposed in the first position with its first end in locking engagement with the first end cap to prevent rotation of the first end cap in the second direction and the removal thereof from the body when the first and second end caps are mounted on the body, the locking means being adapted to be disposed in the second position with its first end disengaged from the first end cap to permit rotation of the first end cap in the second direction and the removal thereof from the body when the second end cap is not mounted on the body.

14. A contact lens disinfection case, which comprises:
a fluid-tight housing, the housing including a cylindrical body having two open ends, and first and second end caps removably mounted on the open ends, the first end cap being threadingly mountable on and removable from the body by rotating the first end cap in opposite tightening and loosening directions, respectively, the first end cap having at least one ramp-like surface and shoulder formed thereon;

means for supporting a contact lens in the housing; and means for selectively locking the first end cap to the body, the locking means having at least one ramp-like surface and shoulder formed thereon, the locking means being selectively positionable within the housing in a first position, wherein the ramp-like surfaces of the first end cap and locking means are adapted to slidably engage each other to allow the first end cap to rotate in the tightening direction, and wherein the shoulders of the first end cap and locking means are adapted to abut against each other to prevent the first end cap from rotating in the loosening direction, and being selectively positionable in a second position, wherein the ramp-like surfaces and shoulders of the first end cap and locking means are in non-engagement respectively with each other to allow the first end cap to rotate in at least the loosening direction, the locking means being positioned in the first position when the second end cap is mounted on the body, and being adapted to be positioned in the second position when the second end cap is not mounted on the body.

* * * * *